US009468386B2

(12) United States Patent
Braojos Lopez et al.

(10) Patent No.: US 9,468,386 B2
(45) Date of Patent: Oct. 18, 2016

(54) METHOD FOR DETECTING ABNORMALITIES IN AN ELECTROCARDIOGRAM

(71) Applicant: ECOLE POLYTECHNIQUE FEDERALE DE LAUSANNE (EPFL), Lausanne (CH)

(72) Inventors: Ruben Braojos Lopez, Lausanne (CH); Giovanni Ansaloni, Bussigny (CH); David Atienza Alonso, Ecublens (CH); Francisco Rincon Vallejos, Renens (CH); Srinivasan Murali, Lausanne (CH)

(73) Assignee: ECOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 14/642,782

(22) Filed: Mar. 10, 2015

(65) Prior Publication Data

US 2015/0257668 A1  Sep. 17, 2015

Related U.S. Application Data

(60) Provisional application No. 61/950,939, filed on Mar. 11, 2014.

(51) Int. Cl.
*A61B 5/04* (2006.01)
*A61B 5/0452* (2006.01)
*A61B 5/00* (2006.01)

(52) U.S. Cl.
CPC ......... *A61B 5/04012* (2013.01); *A61B 5/0452* (2013.01); *A61B 5/7267* (2013.01); *A61B 5/0006* (2013.01); *A61B 5/0024* (2013.01)

(58) Field of Classification Search
None
See application file for complete search history.

(56) References Cited

U.S. PATENT DOCUMENTS

2004/0230105 A1* 11/2004 Geva .................. A61B 5/04012
600/301
2010/0285082 A1* 11/2010 Fernandez ........... A61B 5/0215
424/422

OTHER PUBLICATIONS

Braojos R, Beretta I, Ansaloni G, Atienza D. Early classification of pathological heartbeats on wireless body sensor nodes. Sensors (Basel). Nov. 27, 2014;14(12):22532-51.*

(Continued)

*Primary Examiner* — Brian T Gedeon
*Assistant Examiner* — Ankit D Tejani
(74) *Attorney, Agent, or Firm* — The Law Office of Joseph L. Felber

(57) ABSTRACT

A method for classification of ECG beats into normal and different categories of abnormal beats. The method comprises the following steps, performed on a computing platform:
a. performing a training phase comprising taking as an input one or more ECG beats that are pre-classified into the different categories, with each ECG beat decomposed into multiple features and defining membership functions for each beat category for each feature;
b. performing an operating phase, wherein (i) for each ECG beat to be classified, decompose the ECG beat into the multiple features; (ii) compute values of each membership function identified in the step of performing the training phase for each feature of the ECG beat for the different categories; (iii) merge the membership function values for all features in an ECG beat in a manner as to get a single beat value for each beat category across the features; (iv) identify a value alpha in the range [0,1], such that the difference between the top two beat values across the different beat categories is more than or equal to the sum of the beat values of all the remaining beat categories multiplied by the value alpha and such that a desired percentage of normal or abnormal beat classification is obtained; (v) if an alpha value can be identified, then classify the beat to belong to the beat that has the highest beat value, otherwise classify the beat as abnormal.

19 Claims, 3 Drawing Sheets

(56) References Cited

Figure 1:
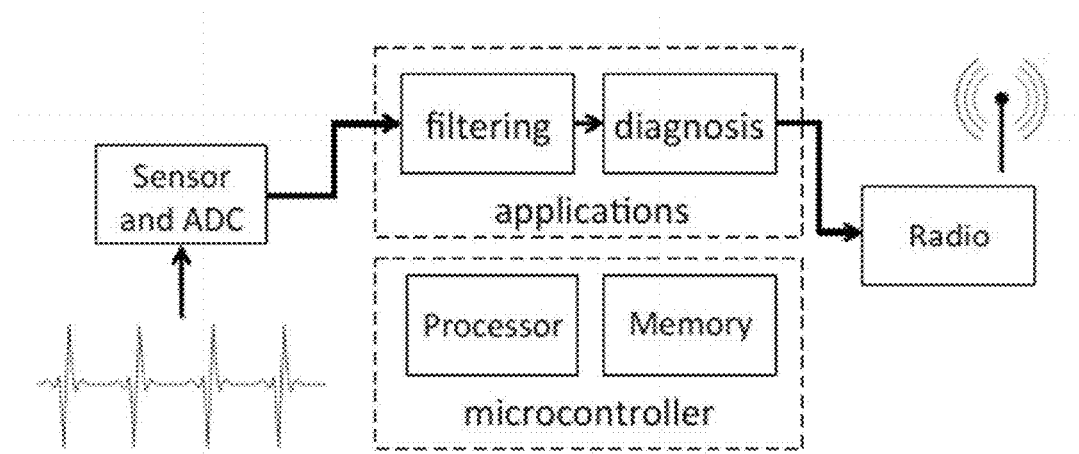

OTHER PUBLICATIONS de Chazal P, O'Dwyer M, Reilly RB. Automatic classification of heartbeats using ECG morphology and heartbeat interval features. IEEE Trans Biomed Eng. Jul. 2004;51(7):1196-206.*

Neagoe VE, Iatan I, Grunwald S. A Neuro-Fuzzy Approach to Classification of ECG Signals for Ischemic Heart Disease Diagnosis. AMIA Annu Symp Proc. 2003; 2003: 4941498.*

Rincón F, Recas J, Khaled N, Atienza D. Development and evaluation of multilead wavelet-based ECG delineation algorithms for embedded wireless sensor nodes. IEEE Trans Inf Technol Biomed. Nov. 2011;15(6):854-63.*

Ye C, Coimbra MT, Vijaya Kumar BK. Arrhythmia detection and classification using morphological and dynamic features of ECG signals. Conf Proc IEEE Eng Med Biol Soc. 2010;2010:1918-21.*

F. Rincon, J. Recas, N. Khaled, and D. Atienza, "Development and evaluation of multilead wavelet-based ECG delineation algorithms for embedded wireless sensor nodes," IEEE Transactions on Information Technology in Biomedicine, vol. 15, No. 6, pp. 854-863, Nov. 2011.

X. Jiang, L. Zhang, Q. Zhao, and S. Albayrak, "ECG arrhythmias recognition system based on independent component analysis feature extraction," 2006 IEEE Region 10 Conference in TENCON 2006, Nov. 2006, pp. 1-4.

R. Ceylan and Y. Ozbay, "Comparison of FCM, PCA and WT techniques for classification ECG arrhythmias using artificial neural network," Expert Systems with Applications, vol. 33, No. 2, pp. 286-295, 2007.

V.-E. Neagoe, I.-F. Iatan, and S. Grunwald, "A neuro-fuzzy approach to classification of ECG signals for ischemic heart disease diagnosis," in American Medical Informatics Association Annual Symposium, 2003, pp. 494-498.

Braojos et al., "A Methodology for Embedded Classification of Heartbeats Using Random Projections," Proceedings of the 2013 Design, Automation, and Test in Europe conference, Grenoble, France, presented Mar. 18-22, 2013.

C.-T. Sun and J.-S. Jang, "A neuro-fuzzy classifier and its applications," Second IEEE International Conference on Fuzzy Systems, vol. 1, 1993, pp. 94-98.

R. Ceylan, Y. Ozbay, and B. Karlik, "A novel approach for classification of ECG arrhythmias: Type-2 fuzzy clustering neural network," Expert Systems with Applications, vol. 36, No. 3, Part 2, pp. 6721-6726, Aug. 2009.

M. F. Moller, "A scaled conjugate gradient algorithm for fast supervised learning," Neural Networks, vol. 6, No. 4, pp. 525-533, (Preprint provided.).

B. Cetisli and A. Barkana, "Speeding up the scaled conjugate gradient algorithm and its application in neuro-fuzzy classifier training," Soft Computing, vol. 14, No. 4, pp. 365-378, Oct. 2009.

P. de Chazal, M. O'Dwyer, and R. Reilly, "Automatic classification of heartbeats using ECG morphology and heartbeat interval features," IEEE Transactions on Biomedical Engineering, vol. 51, No. 7, pp. 1196-1206, Jul. 2004.

S.-N. Yu and K.-T. Chou, "Integration of independent component analysis and neural networks for ECG beat classification," Expert Systems with Applications, vol. 34, No. 4, pp. 2841-2846, May 2008.

I. Guler and E. D. Ubeyli, "ECG beat classifier designed by combined neural network model," Pattern Recognition, vol. 38, No. 2, pp. 199-208, Feb. 2005.

C. Ye, M. Coimbra, and B. Vijaya Kumar, "Arrhythmia detection and classification using morphological and dynamic features of ECG signals," 2010 Annual International Conference of the IEEE in Engineering in Medicine and Biology Society (EMBC), Sep. 2010, pp. 1918-1921.

D. Achlioptas, "Database-friendly random projections: Johnson-Lindenstrauss with binary coins," Journal of Computer and System Sciences, vol. 66, No. 4, pp. 671-687, Jun. 2003.

\* cited by examiner

METHOD FOR DETECTING ABNORMALITIES IN AN ELECTROCARDIOGRAM

FIELD OF THE INVENTION

The present invention relates to a method for abnormal beat detection in an Electrocardiogram (ECG) to detect cardiac arrhythmia and other abnormalities.

BACKGROUND OF THE INVENTION

Wireless Body Sensor Nodes (WBSNs) are miniaturized, wearable systems able to measure and wirelessly transmit biological signals of patients. A major field of application of WBSNs is the ambulatory acquisition of electrocardiograms (ECGs), which evaluates the electrical activity of the heart. In this context, these devices allow long time monitoring of subjects producing little discomfort and requiring minimal medical supervision.

A recent trend in WBSNs, driven by the progress in semiconductor technologies, has been the emergence of "smart" wireless nodes [1]. These smart WBSNs (FIG. 1) can, in addition to acquiring and transmitting data wirelessly, perform advanced digital signal processing filtering noise typically corrupting the signals and/or executing an automated diagnosis.

In the field of ambulatory electrocardiography, an important early diagnosis step is to separate normal and pathological heartbeats. The benefit of this separation is two-fold: first, it can provide helpful information for speeding up the visual inspections of lengthy recordings by medical staff; second, it can be used to activate a more detailed analysis of only those beats presenting pathological characteristics.

The second scenario can lead to two non-obvious, yet substantial, benefits. On the one hand, if a detailed diagnosis is performed off-node, it can be desirable to transmit or store only pathological beats on the WBSN, greatly reducing either the energy employed for wireless transmission or the data storage requirements, respectively. On the other hand, even if the analysis of beats is executed on the wireless node, computation effort can be reduced by activating it only when abnormal beats are detected, increasing energy efficiency.

While off-line algorithms have been proposed to classify the different heartbeat morphologies [2][3], their real-time implementation poses a considerable challenge on WBSN platforms, due to their high computational requirements.

A neuro-fuzzy classifier (NFC) approach [4] is instead potentially a good candidate for this application. Its simple feed-forward structure makes it eligible to be optimized for, and executed on, the constrained resources typically present on WBSNs.

An important factor to consider is the high dimensionality of the heartbeat representation problem as, for every beat, tens of samples before and after the R peak of the QRS complex peak have to be considered to perform a reliable classification.

To effectively address this problem, in the method according to the invention enables to classify ECG beats using a method based on random projections (RPs) that can lead to reduction in input size. The approximation error introduced by random projections is theoretically bounded, nonetheless empirical evidence shows that certain projections perform better than others. Our experiments show that even a rather simple optimization, such as the one performed by a genetic algorithm in few generations, can find a proper projection to obtain optimal classification results. In one embodiment of the invention, the method includes the RP-classifier, a filtering stage and a peak detector, used to isolate beats. In one embodiment, three-lead delineation is used instead adopted as an example of detailed analysis, and is activated by the classifier only for beats identified as pathological.

Test heartbeats were retrieved from the MIT-BIH Arrhythmia database [5], considering all beats presenting three different morphologies: normal sinus rhythms, left bundle branch blocks and premature ventricular contractions. Experimental results show that the proposed methodology can identify more than 97% of abnormal beats, while using a small fraction of the available SoC memory and computing resources.

Neuro-fuzzy classifiers (NFCs) [6] have been extensively studied in the literature. Their ability to explicitly express uncertainty in classification, given by the employed fuzzy values, makes them particularly well suited to the problem of heartbeat classification, as proposed in [7].

NFCs can be effectively trained using established methods, the most common being the gradient descent algorithm described in [6] and the scale conjugate gradient introduced in [8] and [9], which is employed in this work. The approach is both computationally simpler and presenting lower memory requirements than comparable methods, like the ones based on support vector machines [2] and linear discriminants [10]. Therefore, it is more suitable for execution in embedded WBSNs.

Several state-of-the-art strategies for neuro-fuzzy classification of ECGs can be distinguished based on the methodology employed to extract the features of individual heartbeats generating the classifier input. Solutions to the features extraction problem include the ones based on Independent or Principal component analysis (ICA [11]/PCA, [3]), Discrete Wavelets Transform (DWT [12]) and Discrete Cosine Transform (DCT [4]). As opposed to the method disclosed in this invention, these methods demand a computation effort not compatible with WBSN resources.

A different approach, based on detection of morphological features, is presented in [13]; it nevertheless requires a detailed analysis of heartbeats before classification, conversely to our goal of early identification of pathological beats.

SUMMARY OF THE INVENTION

In a first aspect, the invention provides a method for classification of ECG beats into normal and different categories of abnormal beats. The method comprises the following steps, performed on a computing platform a. performing a training phase comprising
   taking as an input one or more ECG beats that are pre-classified into the different categories, with each ECG beat decomposed into multiple features and defining membership functions for each beat category for each feature;

b. performing an operating phase, wherein
   (i) for each ECG beat to be classified, decompose the ECG beat into the multiple features;
   (ii) compute values of each membership function identified in the step of performing the training phase for each feature of the ECG beat for the different categories;
   (iii) merge the membership function values for all features in an ECG beat in a manner as to get a single beat value for each beat category across the features;
   (iv) identify a value alpha in the range [0,1], such that the difference between the top two beat values across the different beat categories is more than or equal to the sum of the beat values of all the remaining beat categories multiplied by the value alpha and such that a desired percentage of normal or abnormal beat classification is obtained;
  (v) if an alpha value can be identified, then classify the beat to belong to the beat that has the highest beat value, otherwise classify the beat as abnormal.

In a preferred embodiment of the invention, the ECG beat is decomposed into multiple features, and the feature set vector is reduced by multiplying the vector by a matrix such that the output is a vector with fewer entries.

In a further preferred embodiment of the invention the matrix is composed such that the entries are randomly assigned a value of $\{+1, -1, 0\}$ with a pre-defined probability values of $\{1/6, 1/6, 2/3\}$.

In a further preferred embodiment of the invention, the method further comprises generating multiple matrices by starting from a set of initial random matrices and using a genetic algorithm; using the newly reduced features in the step of performing the operating phase; and choosing from the generated multiple matrices the matrix that has the best performance in achieving the desired percentage of classification of normal and abnormal beats for the step of performing the operating phase.

In a further preferred embodiment of the invention the step of performing the operating phase is run on an embedded micro-controller, such that the floating point operations involved are converted into integer operations.

In a further preferred embodiment of the invention each of the membership functions is a Guassian function.

In a further preferred embodiment of the invention the step of performing the operating phase is run on an embedded micro-controller, such that the result of the step of merging the membership function values for all features in an ECG beat involves an approximation by a combination of linear functions.

In a further preferred embodiment of the invention exactly four linear functions are used to fit the Gaussian function.

In a further preferred embodiment of the invention the step of merging the membership function values is performed by multiplying the membership values together.

In a further preferred embodiment of the invention the step of merging the membership function values is performed by multiplying the membership values together, and the membership function values are scaled uniformly by a constant value, in order to avoid the multiplied values to reach 0 when converted into integer values when used on an embedded processor.

In a further preferred embodiment of the invention the step of merging the membership function values is performed by multiplying the membership values together, and the membership function values are scaled uniformly by a constant value, in order to avoid the multiplied values to reach 0 when converted into integer values when used on an embedded processor.

In a further preferred embodiment of the invention the scaling by a constant value is achieved by left shifting the binary equivalent of the values across all the membership functions by a constant amount.

In a further preferred embodiment of the invention the scaling by a constant value is achieved by left shifting the binary equivalent of the values across all the membership functions by a constant amount.

In a further preferred embodiment of the invention additional values of fiducial points of an ECG are added to decomposed features.

In a further preferred embodiment of the invention the fiducial points comprise a starting point, a peak or end of P wave, a QRS complex, a R-peak and a T wave of the ECG.

In a further preferred embodiment of the invention distances between the fiducial points are added to a sample space.

In a second aspect, the invention provides a Wireless Body Sensor Nodes device that comprises a code in its memory, that when executed by a processor of the device causes the device to execute a method for classification of ECG beats into normal and different categories of abnormal beats. The method comprising the following steps,
  a. performing a training phase comprising
    taking as an input one or more ECG beats that are pre-classified into the different categories, with each ECG beat decomposed into multiple features
    defining membership functions for each beat category for each feature;
  b. performing an operating phase, wherein
    (i) for each ECG beat to be classified, decompose the ECG beat into the multiple features;
    (ii) compute values of each membership function identified in the step of performing the training phase for each feature of the ECG beat for the different categories;
    (iii) merge the membership function values for all features in an ECG beat in a manner as to get a single beat value for each beat category across the features;
    (iv) identify a value alpha in the range [0,1], such that the difference between the top two beat values across the different beat categories is more than or equal to the sum of the beat values of all the remaining beat categories multiplied by the value alpha and such that a desired percentage of normal or abnormal beat classification is obtained;
    (v) if an alpha value can be identified, then classify the beat to belong to the beat that has the highest beat value, otherwise classify the beat as abnormal.

BRIEF DESCRIPTION OF THE FIGURES AND TABLES

Figure 3:
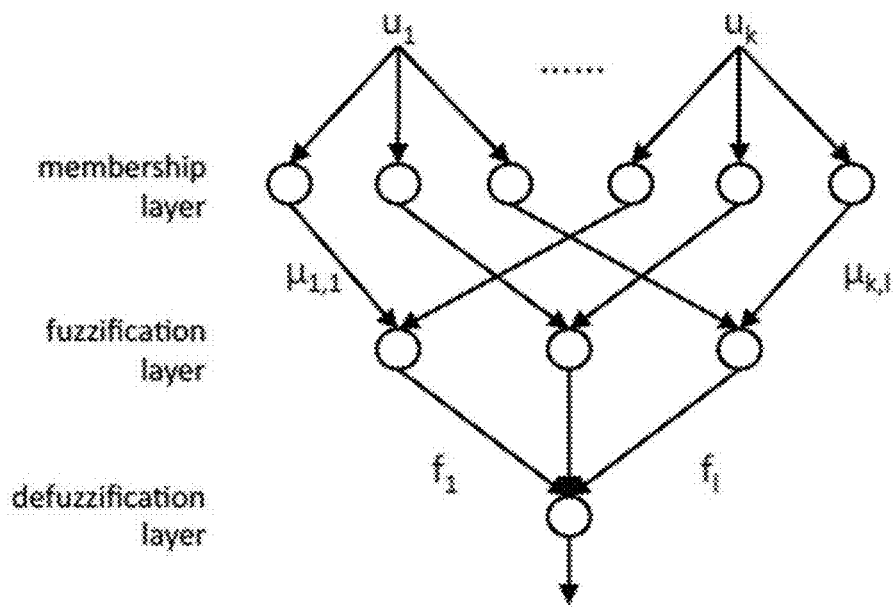
Figure 2:
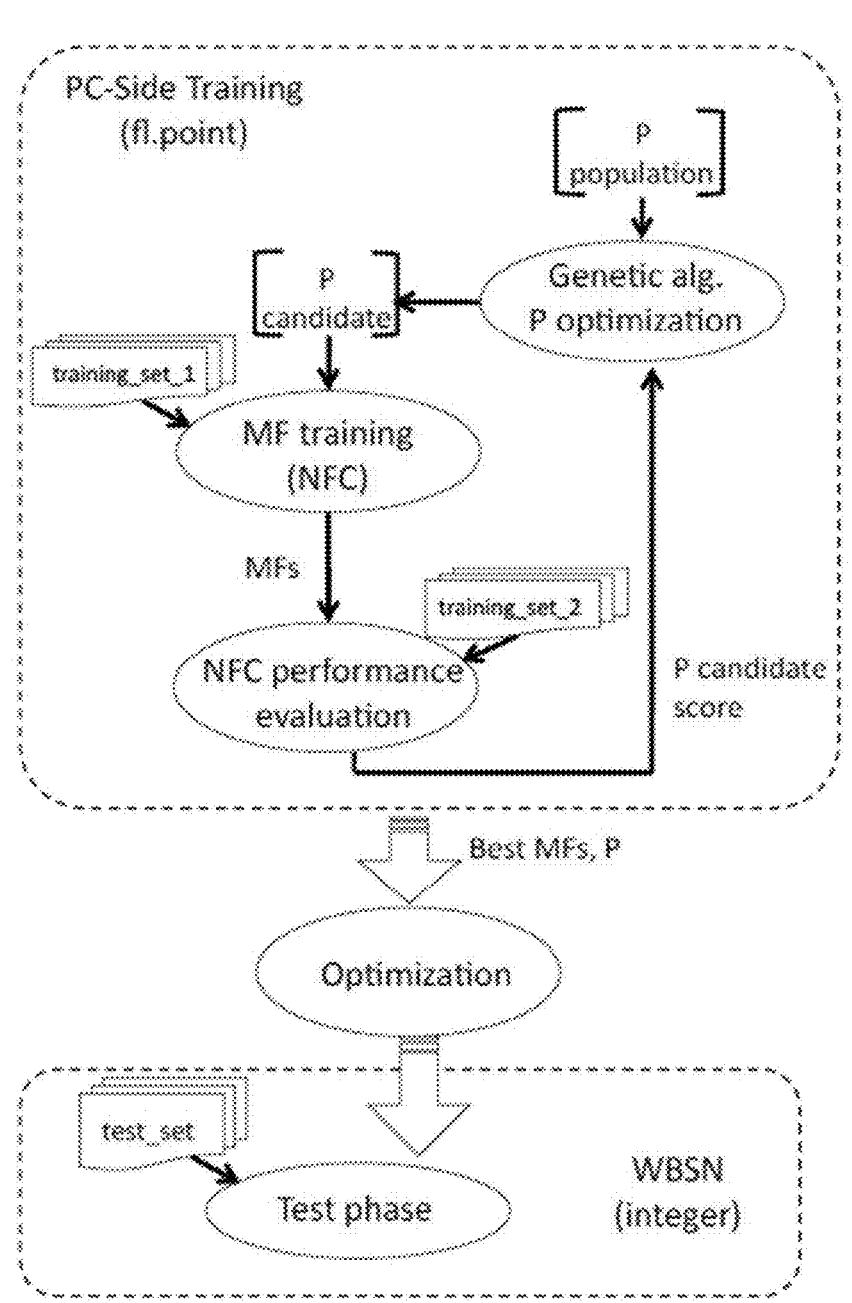
Figure 4:
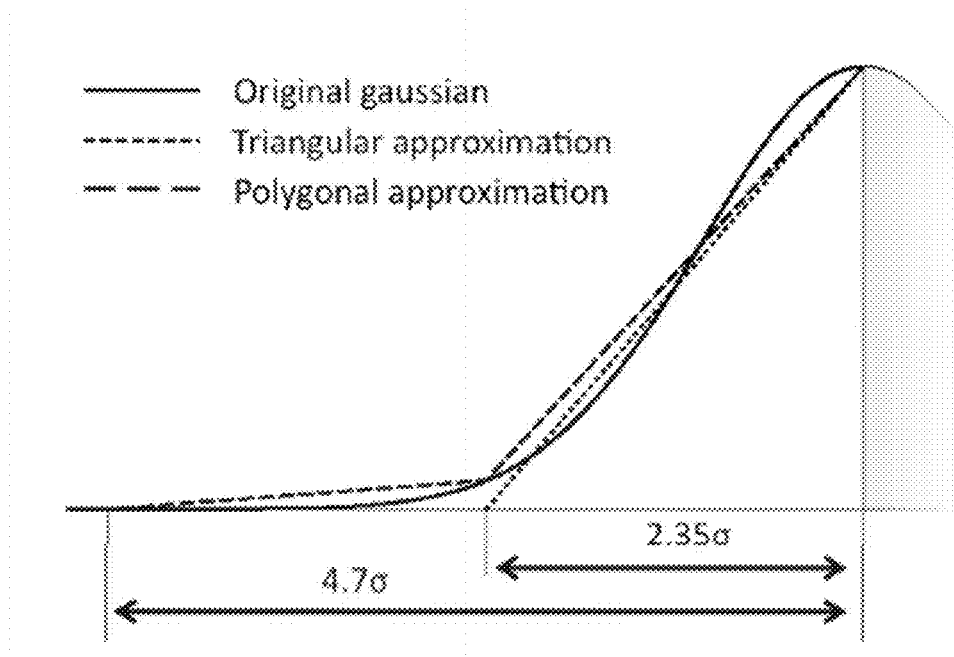
Figure 5:
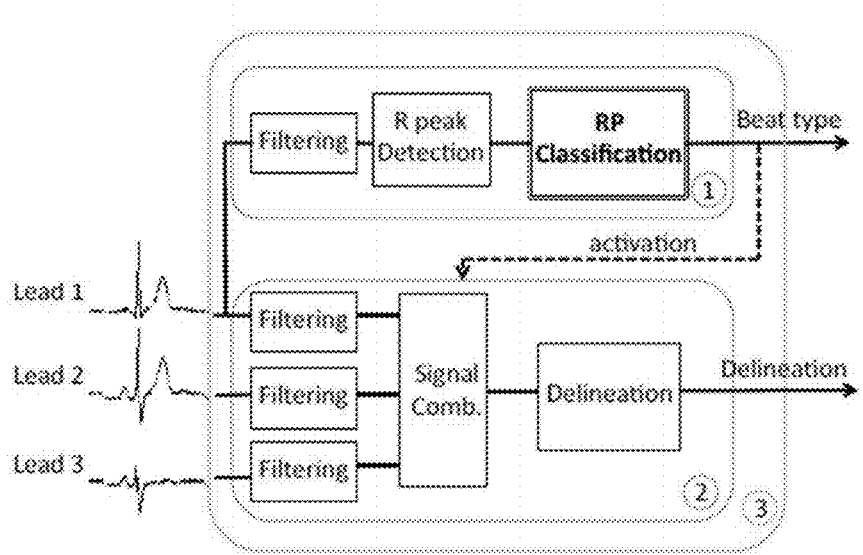

The invention will be better understood from the description of preferred embodiments and in light of the figures and tables, wherein FIG. 1 contains a block scheme of a WBSN platform;

FIG. 2 contains a schematic representation of a Random Projection (RP) based fuzzy classification framework: PC-based training (top) and WBSN execution (bottom);

FIG. 3: illustrates a three layers Neuro-Fuzzy Classifier (NFC);

FIG. 4 contains a graph of a inear approximation of Gaussian MFs;

FIG. 5 illustrates a two-step procedure of beat classification—the second step of activating signal delineation is performed only when an abnormal beat is detected;

table I contains size and composition of the two training sets and of the test set of ECG Heartbeats; and table II contains Normal Discard Rate (NDR) on test_set for a fixed Abnormal Recognition Rate (ARR) of 97%, varying the number of coefficients.

DESCRIPTION OF PREFERRED EMBODIMENTS OF THE INVENTION

The training and test phases of the classification framework, which are illustrated in FIG. 2, have multiple and different constraints. On the one side, the training phase is performed off-line, on a host (PC) platform and using high-precision (floating-point) data representation to obtain the most accurate framework set-up. On the other side, the test phase is executed on an embedded WBSN, being therefore tightly constrained in memory footprint and run-time, admitting only integer arithmetic and avoiding exponential operations.

It is therefore mandatory to transform the classifier, after training and before execution, to lower its computational requirements according to the embedded platform capabilities. The following description details the proposed method to realize this step, the algorithm used for off-line training of the RP matrix and the NFC, and finally, the result of our complete framework that is a classifier which is both accurate and efficient.

A. Training Phase

Random Projection.

The first step of our proposed training phase is the generation of a k×d Achlioptas matrix (P), where d is the number of digital samples acquired for each heartbeat and k is the number of desired coefficients in the random projection, with k<<d. P elements are defined [14] as:

$$P_{k,d} = \begin{cases} +1 & \text{with probability } \frac{1}{6} \\ -1 & \text{with probability } \frac{1}{6} \\ 0 & \text{with probability } \frac{2}{3} \end{cases}$$

Each line of P indicates which elements of an input vector v have to be added (possibly negated) to derive the corresponding vector u of randomly-projected coefficients: u=Pv.

Neuro-Fuzzy Classifier.

The coefficients are the inputs to the multi-layered NFC (FIG. 3). Its first membership layer employs Membership Functions (MFs) to compute, for each coefficient k, a membership grade μ for each of the classes of beats l. In one embodiment of the application, 3 classes are used: normal beats (N), left branch block (L) and premature ventricular contraction (V). The classes can be extended to include several other different beat types, such as atrial fibrillation, ventricular tachycardia, bradycardia and so forth. During the training phase, MFs are gaussian curves, defined by their center c and variance a:

$$\mu_{k,l}(u_k) = \exp\left(\frac{-(u_k - c_{k,l})^2}{2\sigma_{k,l}^2}\right)$$

where $l \in \{N, V, L\}$.

In the subsequent fuzzification layer, the membership grades of all coefficients for each class are multiplied:

$$f_l = \Pi_k \mu_{k,l}.$$

The resulting fuzzy value expresses how strongly an examined heartbeat belongs to that specific class: the larger the value (with respect to the values of the other classes), the higher the confidence in the correctness of the assignment.

The third defuzzification layer of the NFC marks each beat as either normal or pathological, by considering the first and second maximum of the fuzzy values ($M1_f$, $M2_f$) and their sum $$S = \Sigma_{f_l}. \text{ If } (M1_f - M2_f) \geq \alpha_{train} S$$

(with $\alpha_{train}$ in [0, 1]),
, the beat is assigned to the class with maximum fuzzy value (N, V, L). Otherwise, the beat is marked as Unknown (U). V, L, U beats are considered as possibly pathological, while N beats are marked as normal.

The choice of a proper defuzzification coefficient $\alpha_{train}$ gives the flexibility to unbalance the classifier training process, fixing the percentage of abnormal beats incorrectly classified as N. The performance (score) of the trained classifier is then the corresponding percentage of normal beats correctly detected.

Two-Step Training:

The aim of the training is to search for high-performance P matrix and MFs. The algorithm starts from an initial population of random projection matrices $P_{pop}$, optimizing the MFs of the related classifier over a first set of projected heartbeats (training_set 1) using the scale conjugate method [8]. The performance of the random projection is then the score of the associated NFC over a second training set of beats (training_set_2).

In one embodiment, to optimize the projection, we use a genetic algorithm that considers each P in $P_{pop}$ as chromosomes and, performing crossover and mutation operations on them, derive higher-performance candidates. For the experiments presented herein under, we employed an initial population of 20 matrices and let the algorithm run for 30 generations.

B. Resource-Constrained Optimization Phase

The optimized projection and the trained classifier cannot be employed "as they are" in a WBSN platform. A first consideration is that data must be represented as integers, as opposed to the floating point format used in the training phase.

Then, several other elements are particularly critical. First, gaussian MFs employed in the NFC make use of exponential operations, which are not easily (or not at all) implementable in embedded platforms. Second, the NFC fuzzification layer must be analyzed to prevent overflows when performing the product operation. Finally, the memory required to store the random projection matrix can exceed the WBSN resources.

Membership Functions Linearization.

Given their center c and standard deviation σ, gaussian MFs are approximated to the integer range [0, $(2^{16}-1)$] during the optimization step using four segments:

$$MF_{lin}(x) = \begin{cases} 0 & \text{if } |c - x| \geq 4S \\ 1 & \text{if } 4S > |c - x| \geq 2S \\ lin.approx1 & \text{if } 2S > |c - x| \geq S \\ lin.approx2 & \text{if } S > |c - x| \end{cases}$$

where $MF_{lin}$ is the linearized MF and S=2.35σ. The linear approximation segments are graphically represented in FIG. 4. This formulation has the desirable property to be positive in a large range; hence, it is rare that a fuzzy value becomes 0 after the defuzzification (product) classifier stage.

Fuzzification/Defuzzification:

Only the ratio between the fuzzy coefficients $f_l$, as opposed to their value, is relevant for the defuzzification layer. From this observation stems the opportunity to optimize the fuzzification step, retaining the maximum precision given the 32-bit representation used for the results of the defuzzification products. In one embodiment of the application, the membership grades $\mu_{k,l}$ related to the two first coefficients are multiplied for each of the three classes. The three resulting numbers are left-shifted to the maximum amount so that none of them overflow and then the rightmost 16 bits are discarded. All subsequent membership grades are then processed in a similar fashion, obtaining the fuzzy values of the beats for the different classes.

Defuzzification marks each beat as normal or pathological, much like in the training phase. The chosen implementation does not employ divisions, and can therefore be efficiently implemented in WBSNs. Moreover, it is possible to tune the defuzzification coefficient $\alpha_{test}$ independently of the $\alpha_{train}$ chosen during the training phase (described in Section VI-A), giving the opportunity to adjust the ratio of detected normal and abnormal beats.

Random Projection matrix representation. The P matrix is generated in such a way that its elements only assume three values (+1, −1 and 0). In one embodiment, we use a compact representation where each element is coded using two bits, which requires ¼ of the memory with respect to a corresponding matrix of 8-bits values.

Downsampling can also be applied to reduce the memory occupied by the random projection matrix. If, for example, one every four samples of the acquired signal is considered, the size of the matrix is reduced by a factor of four.

EXPERIMENTAL RESULTS

Experimental Setup

To evaluate the proposed RP-based ECG classifier, we investigated its performance when evaluating the normal (N), ventricular contraction (V) and left branch block (L) beats present in the MIT-BIH Arrhythmia Database recordings, available on the Physiobank website [5].

For each beat, classification in either the normal or pathological classes is performed. As mentioned herein above, the goal of the classifier is to recognize abnormal beats, activating only in these cases a detailed analysis such as the three-lead delineation, as shown in FIG. 5. In this context, figures of merit of the classifier are the Normal Discard Rate (NDR) and Abnormal Recognition Rate (ARR). NDR assesses the rate of normal beats that are correctly identified as such and thus discarded.

Complementarily, ARR reports the percentage of abnormal beats that correctly activate the delineation block. Two randomly-selected excerpts of the database where used for training the NFC and optimizing the random projection matrix, respectively. The first training set is smaller than the second because training of the NFC is more computationally complex than its evaluation; in this way, it was possible to retrieve "good" solutions in a reasonable time. The test_set comprises all N, V, L beats present in the database (the composition of the sets is shown in Table I). Across experiments, the defuzzification coefficient $\alpha_{train}$ was chosen to have a minimum ARR of at least 97% on training_set_2.

ECG recordings on the database are acquired at 360 Hz; we define each heartbeat as spanning 100 samples before and 100 samples after its peak. Peaks are automatically detected using a wavelet-based technique, firstly proposed in [1], which decompose the input signals in four dyadic scales at different frequencies, retrieving the peak as the zero-crossing point on the first scale in-between couples of maximum-minimum points across scales.

Evaluation of a Suitable RP Coefficients Number

A first important design choice is to determine the number of random projection coefficients. A larger coefficient set impacts both the size of the random projection matrix and the complexity of the NFC, the decision being therefore a trade-off between classification accuracy and real-time performance (run-time and required memory). To explore this aspect, we trained and tested the framework with a number of coefficients ranging from 8 to 32. Table II reports the NDR corresponding to a minimum ARR of 97% on the test_set. For comparison, the table also presents the classification performance obtained using the off-line Principal Component Analysis (PCA) algorithm proposed in [3] to reduce the representation dimensionality.

Values in the table are classified in three settings. The first row (NDR–PC) refers to a PC-based implementation were no approximation is performed: it therefore uses floating point data representation and gaussian membership functions. The second row (NDR–WBSN) instead shows the performance of the corresponding WBSN version, employing linearized MFs, integer data and a sampling rate of 90 Hz (a four-times downsampling of the original recordings). In the third row (PCA–PC), coefficients are derived from PCA instead of random projections.

Two conclusions can be drawn from these experiments. Firstly, only a small number of randomly-projected coefficients are sufficient to achieve a NDR of over 90%. Actually, increasing this value from 8 to 32 does not benefit classification in a tangible way. Secondly, the difference between NDR–PCA, NDR–PC and NDR–WBSN is rather small, being always in the range of few percentage points. This shows that the proposed methodology does not penalise accuracy, even if the computation effort required in the three cases differs greatly.

Extensions

While the embodiments present beat classification into normal, ventricular contraction and left bundle branch block and unknown categories. The presented methods can be easily extended to detect several other abnormal beat categories as well, by expanding the number of membership functions used, and merging them such that one value is obtained for a beat for each category.

The classifier approach can be extended to handle rhythm abnormalities that are detected based on the distances between the fiducial points. Instead of fitting the samples extracted from the ECG beat to membership functions, in this case, the distance between the ECG fiducial points (such as the length of the PQ segment, QRS complex size and distance, distance of QT, TP, ST, RT segments) can be added as elements to the classifier to build the membership functions. Other information such as the presence or absence or P wave, QRS wave or T wave can also be added of the set of extracted parameters. The parameters could also include abnormal waveforms, such as the inversion of T wave or the presence of a J wave. Many arrhythmias are detected based on the values of these segments or based on the presence/absence of the mentioned waves.

Many ECG abnormalities appear only when multiple beats are analyzed. For example, bradycardia or tachycardia can be detected by finding the distance between consecutive R peaks of two or more ECG beats. The classification method can be easily extended to cover these cases as well. The parameters given to the classifier, apart from the extracted ECG samples and the distance between the fiducuial points, can also include distance between fiducial points across multiple ECG beats (for example, RR interval across two or more beats). The information can also include Heart Rate Variability (HRV) analysis across multiple beats. In fact, the information can also include frequency domain measures (such as the frequency components of RR interval variations), along with the time domain measures. Also, multiple ECG beats can be collected and an ensemble average or a different measure of merging of the ECG beats can be performed, before extracting the samples or the other fiducial point information for the classification process.

REFERENCES

[1] F. Rincon, J. Recas, N. Khaled, and D. Atienza, "Development and evaluation of multilead wavelet-based ECG delineation algorithms for embedded wireless sensor nodes," *Information Technology in Biomedicine, IEEE Transactions on*, vol. 15, no. 6, pp. 854-863, November 2011.

[2] X. Jiang, L. Zhang, Q. Zhao, and S. Albayrak, "ECG arrhythmias recognition system based on independent component analysis feature extraction," in *TENCON 2006. 2006 IEEE Region 10 Conference*, November 2006, pp. 1-4.

[3] R. Ceylan and Y. Ozbay, "Comparison of FCM, PCA and WT techniques for classification ECG arrhythmias using artificial neural network," *Expert Systems with Applications*, vol. 33, no. 2, pp. 286-295, 2007.

[4] V.-E. Neagoe, I.-F. Iatan, and S. Grunwald, "A neuro-fuzzy approach to classification of ECG signals for ischemic heart disease diagnosis," in *American Medical Informatics Association Annual Symposium*, 2003, pp. 494-498. [5] PhysioBank. [Online]. Available: www.physionet.org/physiobank/

[6] C.-T. Sun and J.-S. Jang, "A neuro-fuzzy classifier and its applications," in *Fuzzy Systems, 1993., Second IEEE International Conference on*, 1993, pp. 94-98 vol. 1.

[7] R. Ceylan, Y. Ozbay, and B. Karlik, "A novel approach for classification of ECG arrhythmias: Type-2 fuzzy clustering neural network," *Expert Systems with Applications*, vol. 36, no. 3, Part 2, pp. 6721-6726, August 2009.

[8] M. F. Moller, "A scaled conjugate gradient algorithm for fast supervised learning," *Neural Networks*, vol. 6, no. 4, pp. 525-533, 1993.

[9] B. Cetisli and A. Barkana, "Speeding up the scaled conjugate gradient algorithm and its application in neuro-fuzzy classifier training," *Soft Computing*, vol. 14, no. 4, pp. 365-378, October 2009.

[10] P. de Chazal, M. O'Dwyer, and R. Reilly, "Automatic classification of heartbeats using ECG morphology and heartbeat interval features," *Biomedical Engineering, IEEE Transactions on*, vol. 51, no. 7, pp. 1196-1206, July 2004.

[11] S.-N. Yu and K.-T. Chou, "Integration of independent component analysis and neural networks for ECG beat classification," *Expert Systems with Applications*, vol. 34, no. 4, pp. 2841-2846, May 2008.

[12] I. Guler and E. D. Ubeyli, "ECG beat classifier designed by combined neural network model," *Pattern Recognition*, vol. 38, no. 2, pp. 199-208, February 2005.

[13] C. Ye, M. Coimbra, and B. Vijaya Kumar, "Arrhythmia detection and classification using morphological and dynamic features of ECG signals," in *Engineering in Medicine and Biology Society (EMBC), 2010 Annual International Conference of the IEEE*, September 2010, pp. 1918-1921.

[14] D. Achlioptas, "Database-friendly random projections: Johnson-Lindenstrauss with binary coins," *Journal of Computer and System Sciences*, vol. 66, no. 4, pp. 671-687, June 2003.

The invention claimed is:

1. A method for classification of ECG beats into normal and different categories of abnormal beats, the method comprising the following steps, performed on a computing platform
   a. performing a training phase comprising
      taking as an input one or more ECG beats that are pre-classified into the different categories, with each ECG beat decomposed into multiple features and
      defining membership functions for each beat category for each feature;
   b. performing an operating phase, wherein
      (i) for each ECG beat to be classified, decompose the ECG beat into the multiple features;
      (ii) compute values of each membership function identified in the step of performing the training phase for each feature of the ECG beat for the different categories;
      (iii) merge the membership function values for all features in an ECG beat in a manner as to get a single beat value for each beat category across the features;
      (iv) identify a value alpha in the range [0,1], such that the difference between the top two beat values across the different beat categories is more than or equal to the sum of the beat values of all the remaining beat categories multiplied by the value alpha and such that a desired percentage of normal or abnormal beat classification is obtained;
      (v) if an alpha value can be identified, then classify the beat to belong to the beat that has the highest beat value, otherwise classify the beat as abnormal.

2. The method of claim 1, wherein the ECG beat is decomposed into multiple features, and the feature set vector is reduced by multiplying the vector by a matrix such that the output is a vector with fewer entries.

3. The method of claim 2, wherein the matrix is composed such that the entries are randomly assigned a value of $\{+1, -1, 0\}$ with a pre-defined probability values of $\{\frac{1}{6}, \frac{1}{6}, \frac{2}{3}\}$.

4. The method of claim 2, further comprising
   generating multiple matrices by starting from a set of initial random matrices and using a genetic algorithm;
   using the newly reduced features in the step of performing the operating phase; and
   choosing from the generated multiple matrices the matrix that has the best performance in achieving the desired percentage of classification of normal and abnormal beats for the step of performing the operating phase.

5. The method of claim 3, further comprising
   generating multiple matrices by starting from a set of initial random matrices and using a genetic algorithm;
   using the newly reduced features in the step of performing the operating phase; and
   choosing from the generated multiple matrices the matrix that has the best performance in achieving the desired percentage of classification of normal and abnormal beats for the step of performing the operating phase.

6. The method of claim 1, wherein the step of performing the operating phase is run on an embedded micro-controller, such that the floating point operations involved are converted into integer operations.

7. The method of claim 6, wherein
the step of merging the membership function values is performed by multiplying the membership values together, and
the membership function values are scaled uniformly by a constant value, in order to avoid the multiplied values to reach 0 when converted into integer values when used on an embedded processor.

8. The method of claim 7, wherein the scaling by a constant value is achieved by left shifting the binary equivalent of the values across all the membership functions by a constant amount.

9. The method of claim 1, wherein each of the membership functions is a Guassian function.

10. The method of claim 9, wherein the step of performing the operating phase is run on an embedded micro-controller, such that the result of the step of merging the membership function values for all features in an ECG beat involves an approximation by a combination of linear functions.

11. The method of claim 10, wherein exactly four linear functions are used to fit the Gaussian function.

12. The method of claim 11, wherein
the step of merging the membership function values is performed by multiplying the membership values together, and
the membership function values are scaled uniformly by a constant value, in order to avoid the multiplied values to reach 0 when converted into integer values when used on an embedded processor.

13. The method of claim 12, wherein the scaling by a constant value is achieved by left shifting the binary equivalent of the values across all the membership functions by a constant amount.

14. The method of claim 1, wherein the step of merging the membership function values is performed by multiplying the membership values together.

15. The method of claim 1, wherein additional values of fiducial points of an ECG are added to decomposed features.

16. The method of claim 15, wherein the fiducial points comprise a starting point, a peak or end of P wave, a QRS complex, a R-peak and a T wave of the ECG.

17. The method of claim 15, wherein distances between the fiducial points are added to a sample space.

18. The method of claim 16, wherein distances between the fiducial points are added to a sample space.

19. A Wireless Body Sensor Nodes device that comprises a code in its memory, that when executed by a processor of the device causes the device to execute a method for classification of ECG beats into normal and different categories of abnormal beats, the method comprising the following steps,
   a. performing a training phase comprising
      taking as an input one or more ECG beats that are pre-classified into the different categories, with each ECG beat decomposed into multiple features
      defining membership functions for each beat category for each feature;
   b. performing an operating phase, wherein
      (i) for each ECG beat to be classified, decompose the ECG beat into the multiple features;
      (ii) compute values of each membership function identified in the step of performing the training phase for each feature of the ECG beat for the different categories;
      (iii) merge the membership function values for all features in an ECG beat in a manner as to get a single beat value for each beat category across the features;
      (iv) identify a value alpha in the range [0,1], such that the difference between the top two beat values across the different beat categories is more than or equal to the sum of the beat values of all the remaining beat categories multiplied by the value alpha and such that a desired percentage of normal or abnormal beat classification is obtained;
      (v) if an alpha value can be identified, then classify the beat to belong to the beat that has the highest beat value, otherwise classify the beat as abnormal.

* * * * *